United States Patent [19]

Aagard et al.

[11] Patent Number: 5,389,225
[45] Date of Patent: Feb. 14, 1995

[54] SOLID-STATE OXYGEN MICROSENSOR AND THIN STRUCTURE THEREFOR

[75] Inventors: Roger L. Aagard, Prior Lake; Ulrich Bonne, Hopkins; Barrett E. Cole, Bloomington, all of Minn.

[73] Assignee: Gas Research Institute, Chicago, Ill.

[21] Appl. No.: 875,795

[22] Filed: Apr. 28, 1992

Related U.S. Application Data

[63] Continuation-in-part of Ser. No. 301,017, Jan. 24, 1989, abandoned.

[51] Int. Cl.[6] .................................................. G01N 27/407
[52] U.S. Cl. ........................... 204/426; 204/153.18; 204/408; 204/421; 204/424
[58] Field of Search .................... 204/153.18, 421–429, 204/408

[56] References Cited

U.S. PATENT DOCUMENTS

| 3,464,008 | 8/1969 | Meysson et al. | 204/422 |
|---|---|---|---|
| 3,468,780 | 9/1969 | Fischer | 204/422 |
| 3,719,564 | 3/1973 | Lilly, Jr. et al. | 204/426 |
| 3,914,169 | 10/1975 | Horowitz | 204/427 |
| 3,974,054 | 8/1976 | Poolman et al. | 204/427 |
| 4,040,929 | 8/1977 | Bauer et al. | 204/426 |
| 4,100,048 | 6/1978 | Pompei et al. | 204/415 |
| 4,107,019 | 8/1978 | Takao et al. | 204/426 |
| 4,126,532 | 11/1978 | Takao et al. | 204/426 |
| 4,207,159 | 6/1980 | Kimura et al. | 204/426 |
| 4,210,509 | 7/1980 | Obayashi et al. | 204/426 |
| 4,238,308 | 12/1980 | Kocache et al. | 204/408 |
| 4,244,798 | 1/1981 | Gold et al. | 204/192.15 |
| 4,253,931 | 3/1981 | Gold et al. | 204/192.15 |
| 4,272,329 | 6/1981 | Hetrick et al. | 204/426 |
| 4,272,330 | 6/1981 | Hetrick | 204/426 |
| 4,272,331 | 6/1981 | Hetrick | 204/426 |
| 4,304,652 | 12/1981 | Chiba et al. | 204/425 |
| 4,326,318 | 4/1982 | DeBruin et al. | 422/98 |
| 4,419,213 | 12/1983 | Oshima et al. | 204/425 |
| 4,450,065 | 5/1984 | Yamada et al. | 204/426 |
| 4,487,680 | 12/1984 | Logothetis et al. | 204/426 |
| 4,500,412 | 2/1985 | Takahashi et al. | 204/426 |
| 4,502,939 | 3/1985 | Holfelder et al. | 204/426 |
| 4,505,799 | 3/1985 | Baxter | 204/416 |
| 4,505,806 | 3/1985 | Yamada | 204/426 |
| 4,505,807 | 3/1985 | Yamada | 204/426 |
| 4,510,036 | 1/1985 | Takeuchi et al. | 204/426 |
| 4,521,287 | 6/1985 | Kisner | 204/192.15 |
| 4,559,126 | 12/1985 | Mase et al. | 204/426 |
| 4,587,105 | 5/1986 | Bonne et al. | 204/426 |
| 4,668,374 | 5/1987 | Bhagat et al. | 204/425 |

OTHER PUBLICATIONS

R. J. Ruka, J. E. Bauerle, L. Dykstra, "Seebeck Coefficient of a $(ZrO_2)_{0.85} (CaO)_{0.15}$ Electrolyte Thermocell", *Westinghouse Research Laboratories*, Pittsburgh, Pa., vol. 115, No. 5, pp. 497–501, May 1968.

S. Pizzini, C. Riccardi, V. Wagner, "On the Thermoelectric Power of Stabilized Zirconia", *Reactor Materials Laboratory, Thermochemistry Group*, and C. Sinistri, *Physical Chemistry Department, University of Pavia, Italy*, pp. 559–565, 1970 month unavailable.

Aldo Magistris, Elisabetta Pezzati, Cesare Sinistri, "Thermoelectric Properties of High-Conductivity Solid Electrolytes", Istituto di Chimica Fisica, Universita di Pavia (Italy), vol. 27, #8–9, 1972 month unavailable, pp. 1379–1381.

S. Pizzini, G. Bianchi, "Solid State Electrochemistry II, Devices and Electrochemical Processes", *La Chimica E L'Industria*, vol. 55, No. 12, pp. 967–998, Dec. 1973.

(List continued on next page.)

*Primary Examiner*—T. Tung
*Attorney, Agent, or Firm*—Speckman, Pauley & Fejer

[57] ABSTRACT

A solid-state oxygen microsensor which measures the potential difference (EMF) generated by two spaced apart electrodes deposited on a solid oxygen ion conducting electrolyte and located in a known and preferably constant temperature gradient in the same ambient atmosphere. Output voltage of the sensor is proportional to the temperature gradient established across the electrodes and the unknown oxygen partial pressure of the ambient atmosphere. The solid-state oxygen microsensor is useful for application to systems such as combustion systems to maintain and improve combustion efficiency levels and exhaust gas cleanliness.

15 Claims, 12 Drawing Sheets

OTHER PUBLICATIONS

"Internal-Reference Solid-Electrolyte Oxygen Sensor", David M. Haaland, Analytical Chemistry, vol. 49, No. 12, Oct. 1977.

"Solid State Gas Sensors", P. T. Moseley and B. C. Tofield, Eds., The Adam Hilger Series on Sensors, Adam Hilger, Bristol and Philadelphia, pp. 139–150, 1987 month unavailable.

"Composition, Structure, and ac Conductivity of rf-Sputtered Calcia-Stabilized Zirconia Thin Films", M. Croset, et al., Journal of Applied Physics, vol. 48, No. 2, Feb. 1977.

"Microheater and Microbolometer Using Microbridge of $SiO_2$ Film on Silicon", M. Kimura, Electronics Letters, vol. 17, No. 2, Jan. 22, 1981.

"A Microtransducer for Air Flow and Differential Pressure Sensing Applications", G. B. Hocker, R. G. Johnson, R. E. Higashi, P. J. Bohrer, Workshop on Micromachining and Micropackaging of Transducers, Case Western Reserve University, Cleveland, Ohio, Nov. 7–9, 1984.

F. J. Gutierrez Monreal and G. Vitter, "Measurement of Low Oxygen Pressures with a Solid-State Electrolyte Miniaturised Sensor", J. Phys. E.: Sci Instrum., vol. 16, 1983 month unavailable. Printed in Great Britain.

G. I. Fadeev and M. V. Perfilev, "Thermo-EMF of Cells with a $ZrO_2 + Y_2O_3$ Electrolyte in Atmospheres of Different Compositions", Soc. Electrochem (USA), 894 (1982) month unavailable, (translated from Electrochimya 18, 100 (1982).

Z. S. Volchenkova and N. F. Sizintseva, "The Thermoelectric Force in $ZrO_2$–$Sc_2O_3$, $ZrO_2$–CaO and $ZrO_2$–$Y_2O_3$ Solid Electrolytes", Soc. Electrochem (USA) 13#9, 1190(1977) month unavailable, translated from Electrochimya 13, 1390 (1977).

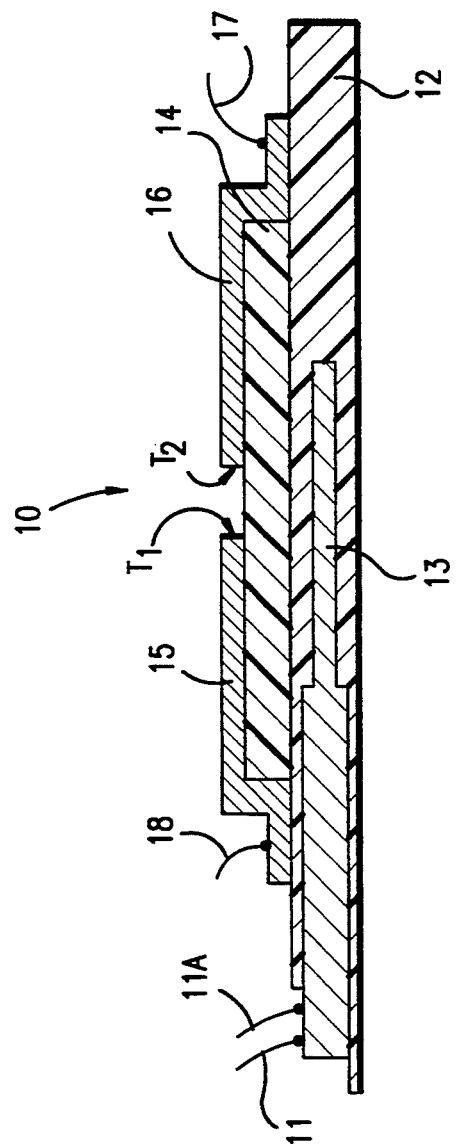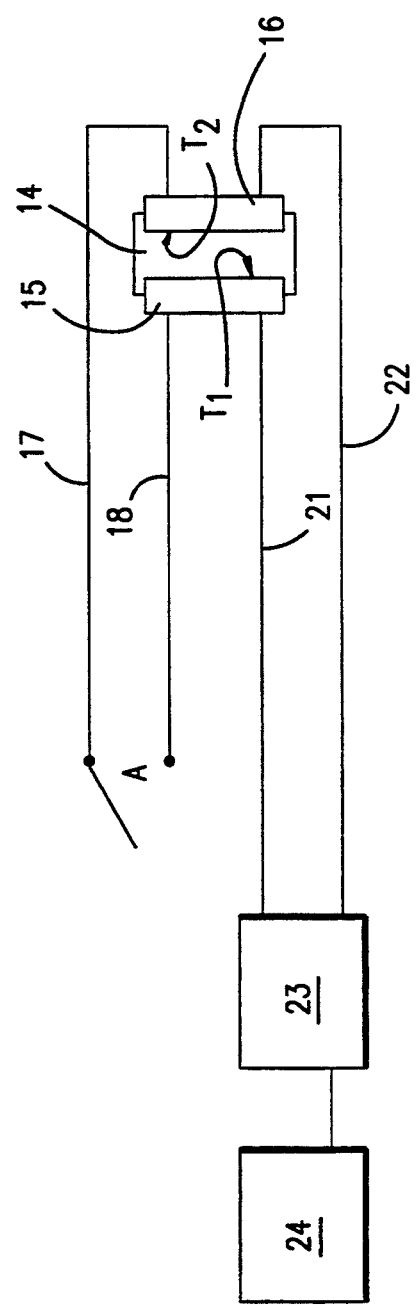

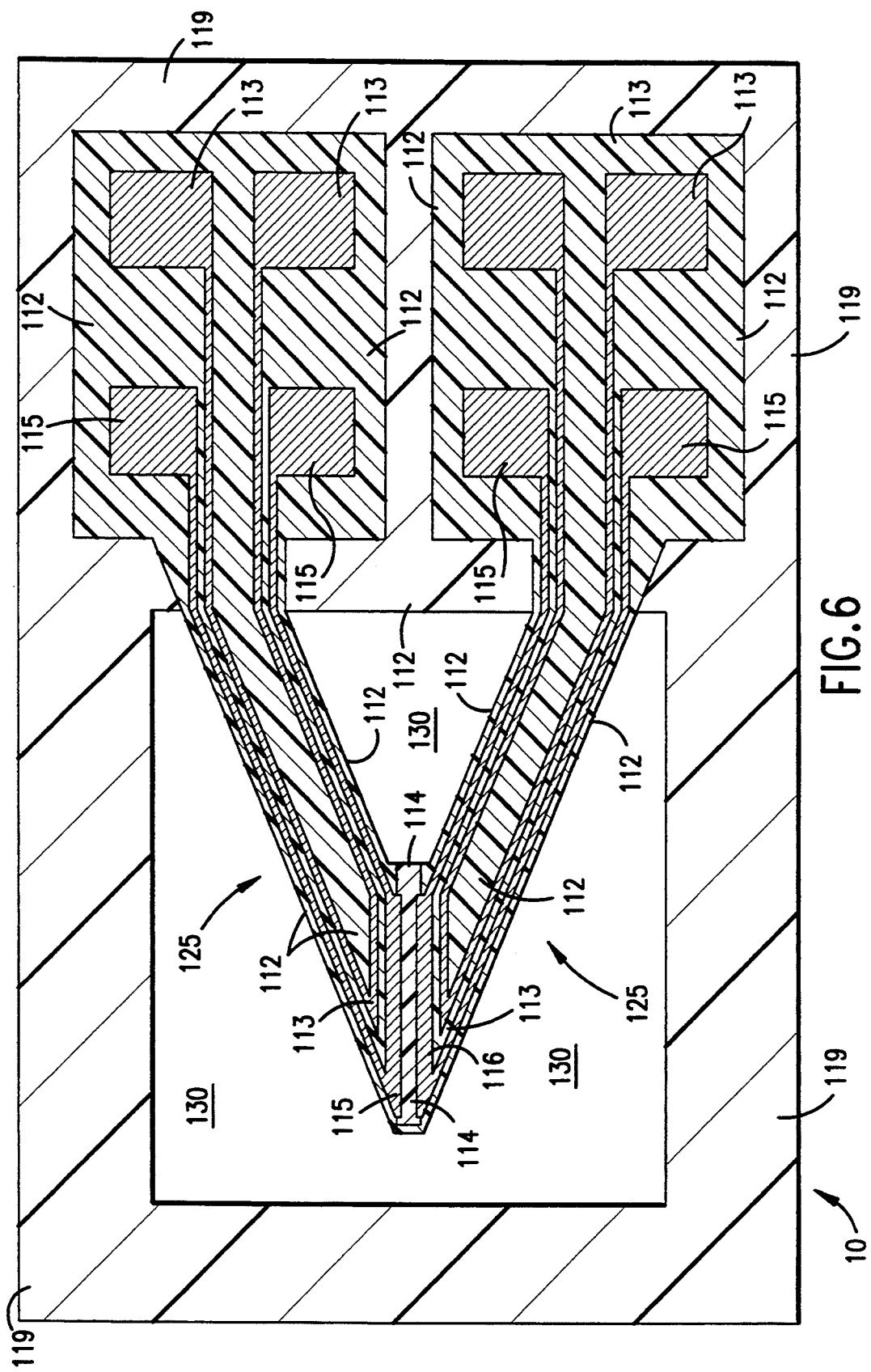

SOLID-STATE OXYGEN MICROSENSOR AND THIN STRUCTURE THEREFOR

CROSS REFERENCE TO RELATED APPLICATION

This patent application is a continuation-in-part of Ser. No. 07/301,017, filed Jan. 24, 1989, now abandoned.

BACKGROUND OF THE INVENTION

1. Field of the Invention

The present invention relates to an absolute, batch processible solid-state oxygen microsensor for use in applications such as combustion systems to maintain and improve combustion efficiency levels. The solid-state oxygen microsensor of the present invention measures the potential difference (EMF) generated by two electrodes deposited on a solid oxygen ion conducting electrolyte and located in a temperature gradient in the same ambient atmosphere. This invention further relates to thin film structural configurations which allow thermal expansion forces to bend or deflect the film into an unconstrained space.

2. Description of the Prior Art

Sensors for determining the oxygen composition of gaseous mixtures, such as automotive exhaust, are well known to the art. For example, U.S. Pat. Nos. 4,272,329, 4,272,330, and 4,272,331 teach an oxygen sensor comprising a pump cell and a sensor cell, each having solid zirconia electrolyte and thin platinum electrodes attached thereto. The sensor cell and the pump cell, along with a ceramic tube, form an enclosed volume in which the ambient air establishes an equilibrium by means of a leak opening in the ceramic tube. The pump cell is connected, by external circuitry, to an electrical input, while the sensor cell is coupled, by external circuitry, to electrical output measurement and control means.

The oxygen sensor taught by the '329 patent is operated in a steady-state mode whereby voltage is applied to the pump cell to electrochemically pump oxygen from the enclosed volume until a steady-state is reached wherein the rate of oxygen pumped from the volume is in equilibrium with the rate of oxygen diffusing into the volume through the leak hole. At steady-state, the oxygen partial pressure in the enclosed volume is reduced from ambient, causing an EMF to develop across the electrodes of the sensor cell. By adjusting the pump cell current continuously to provide a constant sensor cell voltage, the pump cell current is linearly proportional to the percentage oxygen in the ambient atmosphere.

The oxygen sensor taught by the '330 patent uses a similar device operated in a transient mode to measure oxygen partial pressure. After ambient atmosphere of a desired oxygen partial pressure is established in the enclosed volume, the pump cell is activated to withdraw oxygen from the enclosed space. Reduction of oxygen partial pressure in the enclosed space causes an EMF to develop across the sensor cell. The first derivative of sensor cell voltage/time evaluated at or shortly after the initiation of a voltage drop is inversely proportional to the ambient oxygen partial pressure. The oxygen sensor may also be operated by pumping oxygen into the enclosed space and reversing the sign of the initial sensor cell voltage to determine the ambient oxygen partial pressure.

The oxygen sensor taught by the '331 patent uses a similar device operated in an oscillatory mode whereby a repetitive sequence of oxygen pumping currents flow to the pump cell in response to voltage inputs from the sensor cell. The pump cell withdraws oxygen from the enclosed space until the voltage drop induced at the sensor cell equals a predetermined reference value. The polarity of the pump cell current is then reversed to pump oxygen into the enclosed space until the sensor cell voltage reaches another predetermined reference value, at which time the pump cell current is again reversed and the cycle is repeated. With the magnitude of the pump cell current fixed, the period of oscillation is proportional to the oxygen partial pressure.

U.S. Pat. No. 4,510,036 teaches a limiting electric current type oxygen sensor with a microheater formed on an insulating film layer on one of the electrodes. The insulating film limits the amount of oxygen permeated in the electrolyte and electrically insulates the electrolyte from the heater. A small hole is provided in the insulating film to allow permeation of oxygen to the electrolyte. A constant temperature heating control circuit is preferably used to control the heater temperature in accordance with the heater resistance and the electrolyte resistance to obtain a limiting electric current type oxygen concentration detector.

U.S. Pat. No. 4,559,126 teaches an oxygen sensor comprising a plurality of electrolyte layers with electrodes mounted on two of the electrolyte layers and a plurality of ceramic layers with a heater provided in one ceramic layer and a high electric resistance ceramic layer provided between the heater layer and the solid electrolyte layers.

U.S. Pat. No. 4,502,939 teaches an oxygen sensor having electrodes in contact with a solid electrolyte, the electrodes covered with a porous sintered cover layer and a gas tight cover extending over the electrodes and the porous cover layer. Exhaust gases, or the like, are conducted to the sensing electrode, while oxygen from ambient air, or the like, is conducted to the reference electrode through the porous sintered layer. U.S. Pat. Nos. 4,505,806 and 4,505,807 teach an oxygen sensor comprising an oxygen pump cell and an oxygen concentration cell, each having electrodes in parallel alignment on opposite surfaces of solid electrolyte boards, with a ceramic intermediate board having a cavity interposed between the oxygen pump and concentration cells providing communication to the ambient atmosphere. As the oxygen sensor is selectively heated, the oxygen concentration cell measures a ratio of oxygen concentration in the cavity to oxygen concentration of the ambient atmosphere outside the sensor, while the oxygen pump provides diffusion of oxygen between the cavity and the ambient outside atmosphere.

U.S. Pat. Nos. 4,040,929 and 4,107,019 teach the use of thin film electrolytes. The '929 patent teaches a thin film electrolyte such as yttria-stabilized zirconia sputtered onto a substrate layer to form a film about 0.030 to 1.50 microns thick which provides an oxygen sensor capable of operating at temperatures below about 2000° C. The '019 patent teaches the use of a thin film electrolyte supported on a non-conductive base plate and a thin film heater in a metal/metal oxide oxygen concentration cell system. U.S. Pat. No. 4,500,412 teaches an oxygen sensor with a heater layer about 0.2 to 20 microns thick formed on an insulating substrate and covered by a protective layer about 0.01 to 500 microns thick.

Several prior art patents relate to sputtering methods for depositing thin film electrode and electrolyte layers. U.S. Pat. No. 4,244,798 teaches a method for sputtering a porous, high surface area platinum film electrode onto a zirconia thimble. U.S. Pat. No. 4,253,931 teaches another sputtering process for depositing a platinum electrode onto a zirconia thimble in a specified atmosphere at specified pressures. U.S. Pat. No. 4,521,287 teaches yet another sputtering process for depositing high surface area platinum electrode films on a zirconia thimble for use as an exhaust gas oxygen sensor.

U.S. Pat. No. 4,419,213 relates to an oxygen concentration cell formed as a laminate of a plurality of thin layers, including solid electrolyte, supported on a ceramic substrate. A heater is embedded in the ceramic substrate layer and heater lead wires are insulated from concentration cell lead wires by the ceramic substrate to prevent leakage of the heater current. U.S. Pat. No. 4,450,065 teaches an oxygen sensor comprising a pump cell and an oxygen concentration cell, each having a solid electrolyte layer and electrodes deposited thereon. The two cells are coupled in parallel leaving a gap between the two cells. The oxygen concentration cell measures the ratio between oxygen concentration in the gap and oxygen concentration of gas outside the sensor, while the pump cell diffuses oxygen between the gap and the outside atmosphere. U.S. Pat. No. 4,487,680 teaches an oxygen pumping device having two electrolyte layers which may have different porosities and which contact one another, and three electrodes which function to provide both oxygen pump and sensor cells. This oxygen sensor does not require an enclosed volume and can be produced at low cost by conventional planar layer technology.

U.S. Pat. No. 4,126,532 utilizes a metal/metal oxide sinter as a reference oxygen source supported on a base member with a solid electrolyte layer and another electrode to provide an oxygen sensor in which an EMF is developed across the electrodes at relatively low temperatures. U.S. Pat. No. 4,207,159 teaches an oxygen sensor having a probe comprising a porous, conductive reference electrode adjacent a solid electrolyte layer with a similar porous separator layer on the exterior surface of the reference electrode whereby the reference electrode is in communication with the exterior atmosphere through the porous layer. During measurement, current flows through the electrolyte to maintain a reference oxygen partial pressure at the interface between the electrolyte and the reference electrode.

U.S. Pat. No. 4,326,318 teaches an oxygen sensor for measuring oxygen partial pressures which relies upon detection of a thermodynamic transition temperature which interfaces a high resistivity mode and a low resistivity mode. A variable potential is applied across two electrodes separated by a conductive electrolyte, and the resistance between the first electrode and a third electrode isolated from the second electrode is monitored to determine the thermodynamic transition temperature, from which the oxygen partial pressure in atmosphere at a known temperature is determined.

Solid electrolyte oxygen sensors are known which generate an internal oxygen reference, thereby eliminating the conventional oxygen reference. "Internal-Reference Solid-Electrolyte Oxygen Sensor", David M. Haaland, Analytical Chemistry, Vol. 49, No. 12, October 1977. A sensor cell monitors the ratio of oxygen partial pressure inside and outside the sensor, while the other cell functions as a pump. The internal oxygen reference is generated by pumping oxygen from a known cavity volume and then pumping oxygen back into the cavity until the oxygen partial pressure equilibrates.

It is known in the art that combustible gases can be sensed by hot-wire catalytic sensors and metal oxide semiconducting sensors, which change conductivity when exposed to combustible gases to $H_2O$, $CO_2$ or $O_2$, as well as by exposing a two metal semiconductor junction pair to a combustible gas in such a way that one junction having no combustion catalyst remains at a constant temperature and the other junction having a combustion catalyst experiences a small temperature rise due to released heat of combustion. Such a temperature difference output is registered and calibrated in terms of gas concentration. "Solid State Gas Sensors", P. T. Moseley and B. C. Tofield, Eds., The Adam Hilger Series on Sensors, Adam Hilger, Bristol and Philadelphia, pgs. 139-150, 1987.

Several prior art literature references known to the inventors relate to solid-state oxygen microsensor technology and materials. Researchers have demonstrated experimentally that conductivity in calcia-stabilized zirconia thin films deposited by rf sputtering is due to oxygen anion migration. "Composition, Structure, and ac Conductivity of rf-Sputtered Calcia-Stabilized Zirconia Thin Films", M. Croset, et al, Journal of Applied Physics, Vol. 48, No. 2, Feb. 1977. Fabrication of microbridges of $SiO_2$ film over a cavity etched into a silicon chip is described in an article entitled "Microheater and Microbolometer Using Microbridge of $SiO_2$ Film on Silicon", M. Kimura, Electronics Letters, Vol. 17, No. 2, Jan. 22, 1981. Techniques for micromachining silicon structures and fabricating thin film structures are known to provide temperature sensitive resistors which are thermally isolated from the silicon chip. Locally high temperatures may thus be achieved with very low power output and reduced heat losses to the chip. "A Microtransducer for Air Flow and Differential Pressure Sensing Applications", G. B Hocker, R. G. Johnson, R. E. Higashi, P. J. Bohrer, Workshop on Micromachining and Micropackaging of Transducers, Case Western Reserve University, Cleveland, Ohio, Nov. 7-9, 1984.

Prior art oxygen microsensors utilizing an oxygen ion conducting solid electrolyte require either providing and pumping a cavity which involves slow time constants, measuring resistance-dependent values which tend to be drifty, provision of reference gas chambers, observation of metal-metal oxide redox reactions, or complex electronic circuitry. Prior art Nernstian oxygen sensors also require that the electrodes be maintained in a constant temperature environment to avoid false signals generated by thermocouple-like operation.

Prior art oxygen sensing, utilizing the known Seebeck (i.e. thermocouple) effect, in a bulky arrangement involving electrodes at a difference in temperature, both exposed to the same oxygen concentration, is described by Pizzini et al. in "Solid State Electrochemistry II, Devices and Electrochemical Processes", La Chimica E L'Industria, Vol. 55, No. 12, p. 966, December 1973.

Existing thin film oxygen sensors having bridge or diaphragm connections to a substrate thermally expand and tend to severely deform at elevated temperatures thus often resulting in fractures.

SUMMARY OF THE INVENTION

It is an object of the present invention to provide a solid-state absolute oxygen microsensor for reliable and accurate measurement of the oxygen partial pressure in ambient atmosphere which has a simplified configuration; is batch processible; and has low energy requirements.

It is yet another object of this invention to provide a solid-state oxygen microsensor having a thin film structural configuration which allows for bending or deflection, due to thermal expansion forces, into an unconstrained space.

It is yet another object of the present invention to provide a solid-state oxygen microsensor which does not require providing or pumping a cavity, reference gas chambers, measurement of resistance-dependent values, observation of metal-metal oxide redox processes, or relatively complex electronics.

It is yet another object of the present invention to provide a process for measuring the oxygen partial pressure in ambient atmosphere by maintaining a temperature gradient across two electrodes located in the same ambient atmosphere.

The Nernstian potential of the prior art types of solid-state oxygen microsensors is generated by the difference in chemical potential at two electrodes in a constant temperature environment due to differences in the composition of the ambient atmospheres at the electrodes, as follows:

$$E_1 = RT_1/(nF)\ln(a_1); \text{ and}$$

$$E_2 = RT_2/(nF)\ln(a_2)$$

where $R = 8.3144$ J/(K mole);
$T_1, T_2$ = temperature at each electrode;
$n = 4$, the charge transfer number for oxygen;
$F = 96{,}500$ Frard, the charge of one mole of monovalent ions; and
$a_1, a_2$ = chemical activity of oxygen at each of the electrodes which, in conventional practice with $T_1 = T_2$, represents the oxygen partial pressure; however $a_1$ and $a_2$ are also temperature dependent. A measurable, non-zero $EMF = E_1 - E_2$ arises when the chemical activity, or the partial pressure of oxygen, at the two electrodes located in different ambient atmospheres is unequal. A direct relation between the two partial pressures may be obtained, for $T = T_1 = T_2$, according to the following equation:

$$EMF = RT/(nF)\ln(P_1/P_2).$$

According to the practice of the present invention, both electrodes are located in the same composition ambient atmosphere having the same oxygen partial pressure, while a temperature gradient is established across the electrodes. A measurable, non-zero EMF output generated according to the present invention has the following relation:

$$EMF/T = A + R/F(1/2 \ln x_v + 5/8 \ln T + 1/4 \ln p) + Q/(2R\cdot T) + E_1$$

where
$A = -(0.715 \pm 0.018)$mV deg. K
$R = 8.3144$ J/(K mole)
$F = 96{,}500$ coulomb
$x_v$ = mole fraction of free vacancies not combined into complexes
$T$ = Temperature
$p$ = oxygen partial pressure in atmospheres
$Q$ = heat of transport of oxygen ions in the oxide
$E_1$ = EMF of wire contacts to ceramic.

Further details of derivation and use of the above relations may be found in Volchenkov, Z. S. and N. F. Sizintseva, "The Thermoelectric Force in $ZrO_2$—$Sc_2O_3$, $ZrO_2$—$CaO$ and $ZrO_2$—$Y_2O_3$ Solid Electrolytes", Soc. Electrochem (USA) 13#9, 1190 (1977), (transl. from Electrochimya 13, 1390 (1977); Fadeev, G. I. and M. V. Perfilev, "Thermo-EMF of Cells with a $ZrO_2$ + $Y_2O_3$ Electrolyte in Atmospheres of Different Compositions", Soc. Electrochem (USA) 18#7, 894 (1982), (transl. from Electrochimya 18, 1004 (1982)); and Chebotin, V. N., S. L. Firdman and S. F. Pal'quer, Electrokhimiya 6, 1300 (1970); and V. N. Chebotic, M. V. Perfilev, "The Electrochemistry of Solid Electrolytes", Khimiya, Moscow (1978) (in Russian). Because the electrodes are provided in the same composition ambient atmosphere and measurement of a reference gas is unnecessary, the oxygen microsensor apparatus of the present invention may embody a simplified solid-state thin film layered or co-planar design.

The solid-state oxygen microsensor of the present invention comprises an oxygen-ion conducting solid electrolyte; a pair of sensor electrodes located in the same ambient atmosphere and contacting the electrolyte; a heater for heating the microsensor assembly to suitable operating temperatures and for providing a temperature gradient across the electrodes; and means for measuring the EMF output generated during operation of the sensor. The temperature difference between the two electrodes may be measured by a thermocouple composed of two junctions, one at each of the electrodes. Alternatively, if the temperature gradient can be stabilized, measurement of the temperature gradient may be unnecessary. The absolute temperature at the electrodes is quite unimportant, as long as the temperature is within the preferred operating range to provide high oxygen-ion conductivity at the solid electrolyte, and a measurable temperature gradient is maintained across the electrodes. While the sensor impedance changes with absolute temperature, the sensor output does not change significantly with absolute temperature, provided that the measuring device impedance is 30 to 100 times greater. Changes in absolute temperature at each of the electrodes does not significantly influence the output signal, as long as the temperature difference is maintained constant. Similarly, the electrode geometry does not influence the output provided that a constant temperature difference is maintained. Since the electrodes are provided in the same ambient atmosphere, the solid-state oxygen microsensor of the present invention may be further simplified in that the electrodes may be deposited on the same surface of the solid electrolyte, leaving the opposite electrolyte surface free for deposition of a heater.

BRIEF DESCRIPTION OF THE DRAWINGS

Further features of this invention will be apparent from the following more detailed description taken in conjunction with the drawings, wherein:

FIG. 1 shows a cross-sectional view through a solid-state oxygen microsensor according to the present invention;

FIG. 2 shows a basic electrical schematic diagram of a solid-state oxygen microsensor assembly of the present invention;

FIGS. 6-8 show enlarged plan views of the solid-state oxygen microsensor, with the heater and electrode elements exposed for purposes of drawing clarity, utilizing different embodiments of a generally V-shaped or U-shaped thin film structural configuration;

DESCRIPTION OF PREFERRED EMBODIMENTS

Figure 3A:
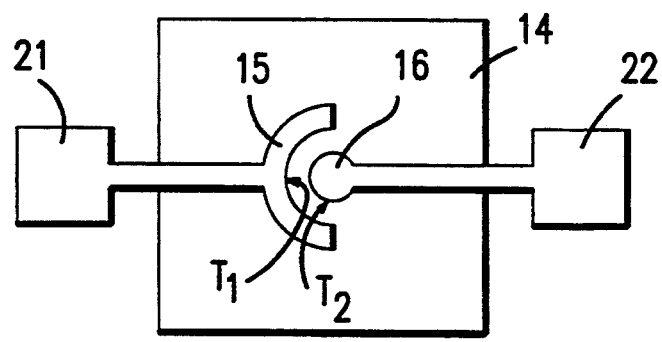
FIG. 3A shows an enlarged plan view of one preferred geometrical arrangement of electrodes over a layer of solid electrolyte, according to one preferred embodiment of this invention.

The solid-state oxygen microsensor of the present invention preferably comprises a layered structure, as shown in the enlarged cross-sectional view of FIG. 1. According to one preferred embodiment of this invention, solid-state oxygen microsensor 10 comprises oxygen ion conducting solid electrolyte 14 with at least two spaced electrodes 15 and 16 in contact therewith, and heater film 13. Heater film 13 is capable of providing high operating temperatures at electrodes 15 and 16, such as on the order of about 300° C.-900° C., and is configured to provide a measurable and preferably constant temperature gradient across electrodes 15 and 16. Electrodes 15 and 16 are spaced apart from one another so that they do not contact each other and are connected by leads 21 and 22, respectively, to an external temperature differential measuring circuit, such as high impedance voltmeter 23 and/or processor 24, as shown in FIG. 2. Heater film 13 is energized at terminals 11 and 11A from an external circuit, known to those skilled in the art. Heater film 13 may be mounted or embedded in dielectric layer 12 of oxygen microsensor 10, to insulate heater film 13 from interaction with electrodes 15 and 16. Oxygen microsensor 10 may also form a bridge structure spanning a depression, or etch pit 130 as shown in FIGS. 6-9A, in support structure 119.

Electrodes 15, 16, 115 and 116 preferably comprise platinum, palladium, rhodium, iridium or other metals or metallic alloys having a relatively high melting temperature and which are capable of catalyzing the dissociation and ionization of oxygen. Electrodes 15, 16, 115 and 116 preferably comprise thin films which may be deposited on solid electrolyte 14 and 114 by means known within the art, such as ion beam sputtering techniques. Each pair of independent sensor electrodes 15 and 16, and 115 and 116 are preferably co-planar with respect to each other, as best shown in FIGS. 1, 2 and 9A. As used throughout this specification and in the claims, the term "co-planar" is intended to mean that independent sensor electrodes 15, 16, 115 and 116 are generally positioned within the same plane. It is apparent that electrode 15, 115 may have a slightly different thickness than electrode 16, 116 or be slightly offset with respect to electrode 16, 116 and such arrangements are intended to be generally described as "co-planar".

Figure 3B:
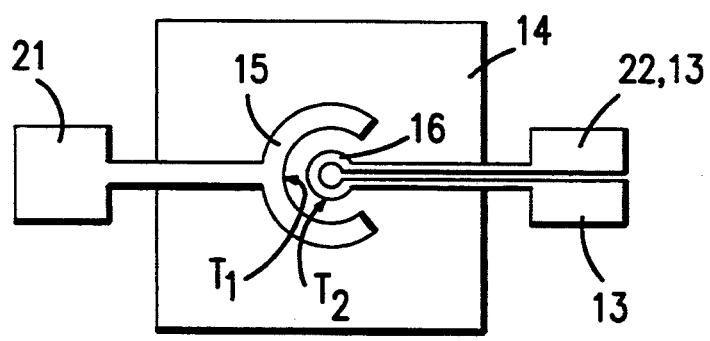
FIG. 3B shows an enlarged plan view of another preferred geometrical arrangement of electrodes over a layer of solid electrolyte, in which one electrode has a dual role as an electrode and a heater, according to another preferred embodiment of this invention.

Many different electrode configurations may be used in the oxygen microsensor of the present invention, but the configurations shown in FIGS. 2, 3A and 3B are preferred. FIG. 2 shows electrodes 15 and 16 having a substantially rectangular or linear configuration. FIG. 3A shows one preferred radial configuration for electrodes 15 and 16. FIG. 3B shows another preferred radial configuration for electrodes 15 and 16, wherein electrode 16 has an overall circular shape and also functions as a heater, while electrode 15 has a concentric semi-circular or arcuate shape surrounding a portion of the circular electrode 16. As shown in FIGS. 2, 3A and 3B, the distance between an internal surface edge at $T_1$ of electrode 15 and an external surface edge at $T_2$ of electrode 16 remains constant, so that the temperature gradient ($T_2-T_1$) remains constant at all points along such internal surface edge and such external surface edge. Electrode 16 preferably operates at a higher temperature than electrode 15, during oxygen microsensor 10 operation, according to this preferred embodiment.

FIGS. 6-9 show plan views of various thin film oxygen microsensors 10 according to preferred embodiments of this invention. In FIGS. 6-9, heaters 113 and sensor electrodes 115 and 116 are shown as exposed metal films, with separate but co-planar films and contact pads for heaters and electrodes. The crosshatch lines in FIGS. 6-9 are primarily for purposes of drawing clarity. It is apparent that oxygen microsensor 10 of this invention can operate either with such elements exposed to the surrounding ambient or with such elements covered with respect to the surrounding ambient.

Figure 4A:
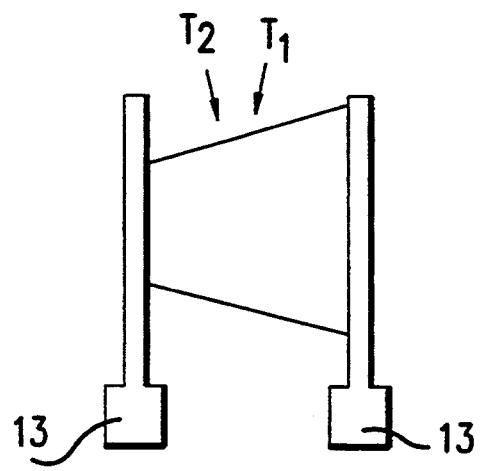
FIGS. 4A-4F show preferred heater configurations for use in the solid-state oxygen microsensor according to this invention.
Figure 4B:
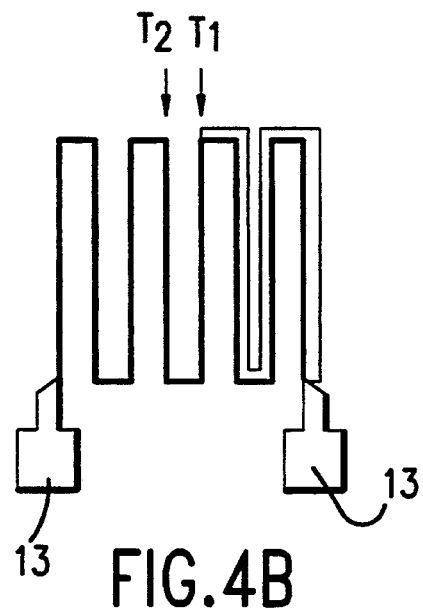
Figure 4C:
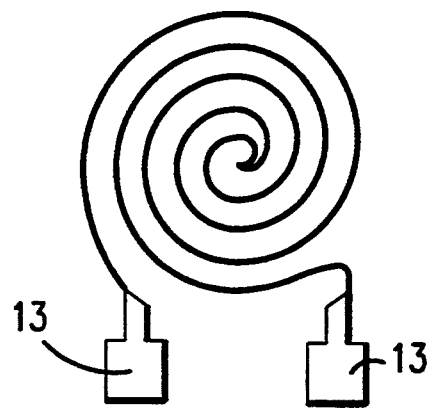
Figure 4D:
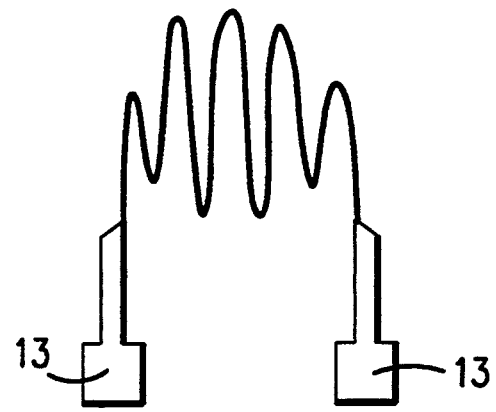
Figure 4E:
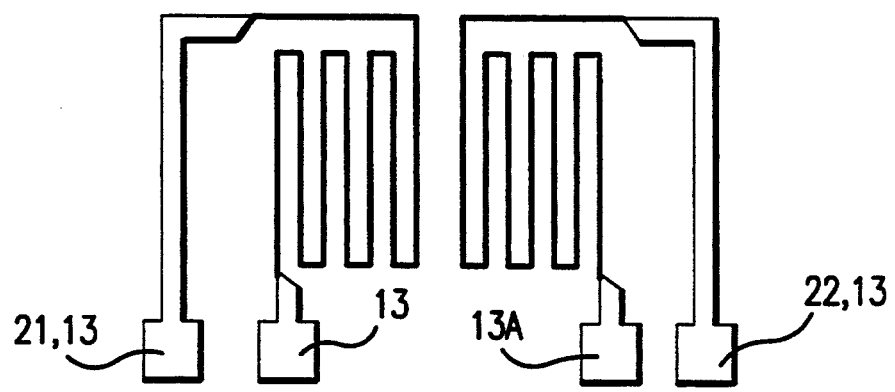
Figure 7:
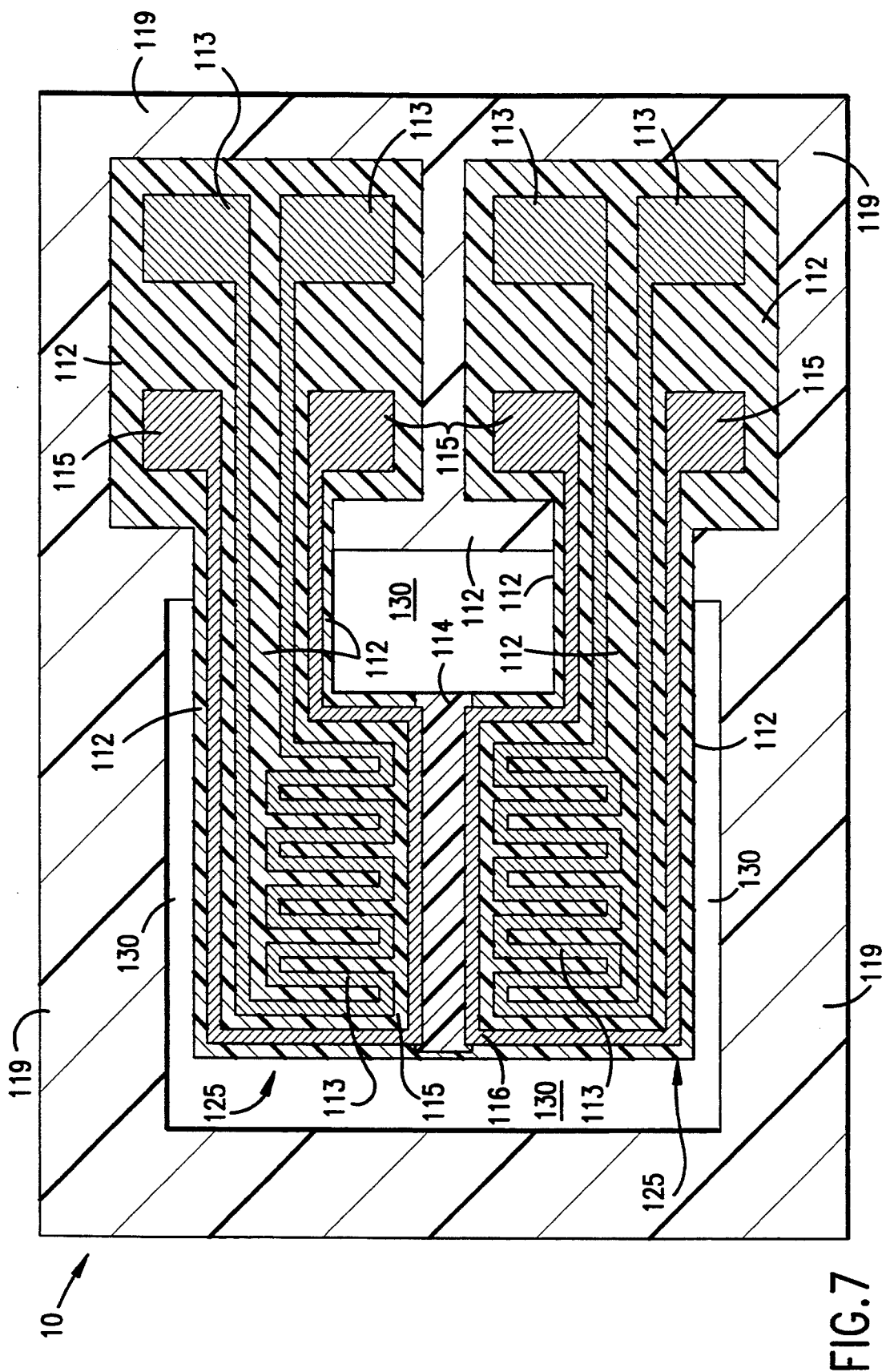
Figure 8:
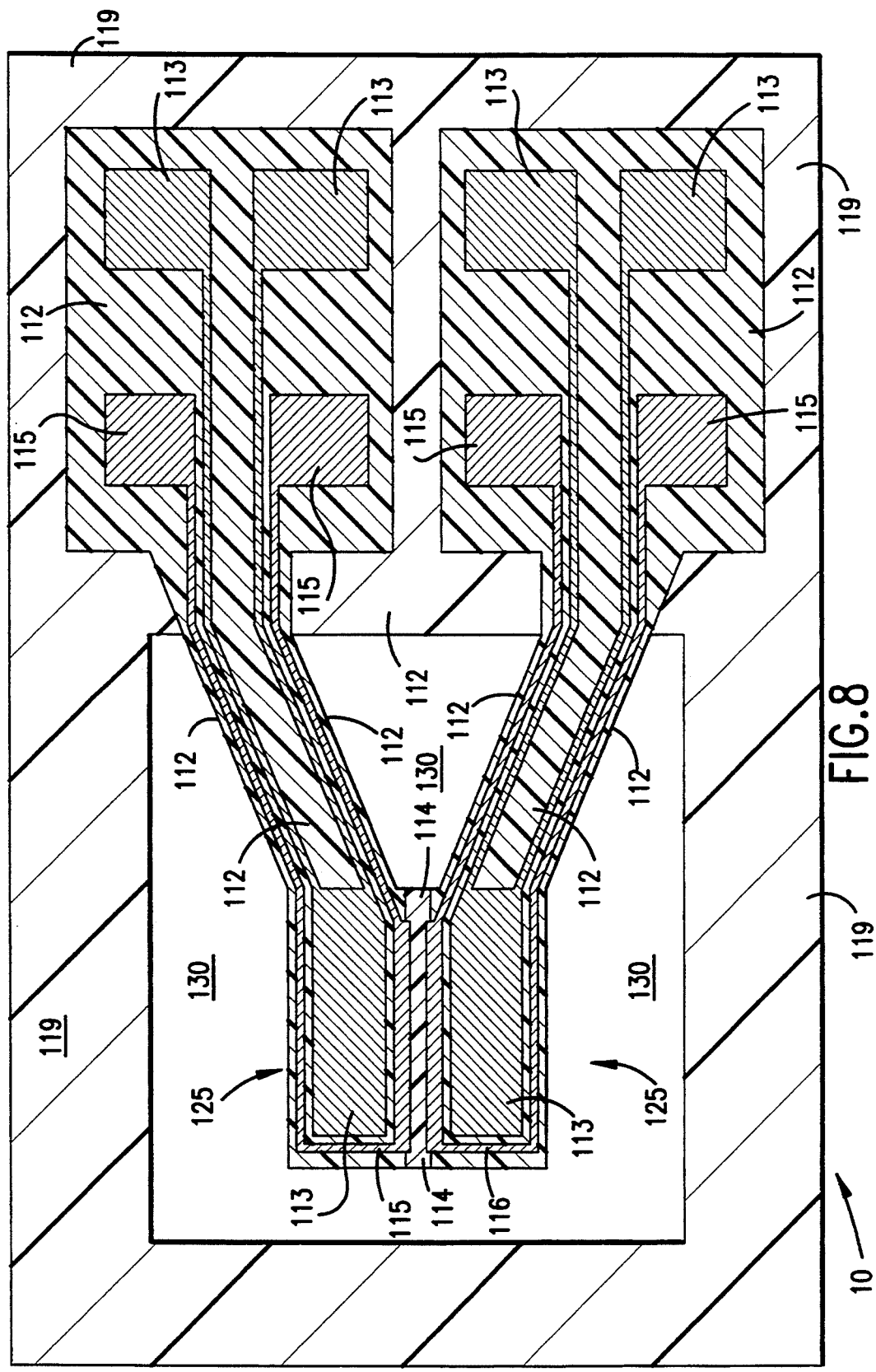

Dielectric layer 112 is mounted on support structure 119 in any suitable manner known to those skilled in the art. Dielectric layer 112 is fixed at one end and has an opposite free end, shown on the left portion of each of FIGS. 6-8, which extends as cantilever portion 125 over etch pit 112. As best shown in FIGS. 6 and 8, dielectric layer 112 has an overall V-shaped structure which forms cantilever portion 125 that extends over etch pit 130. Etch pit 130 is preferably formed by a method such as anisotropic etching or the like, after patterning dielectric layer 112 as shown in FIGS. 6-9. Electrodes 115 and 116 are deposited and patterned to contact and preferably overlap the edges of solid electrolyte 114 and are thus used for measuring the temperature and oxygen potential on each side of solid electrolyte 114. As best shown in FIGS. 6-9, dielectric layer 112 supports solid electrolyte 114 over etch pit 130. Heater films 113 are preferably located on either side of solid electrolyte 114, as shown in FIGS. 6-9, and are supplied with current to maintain a desired and preferably constant temperature gradient across solid electrolyte 114, which is sensed by the change in resistance of either heater films 113 or electrodes 115 and 116. In another preferred embodiment of this invention, electrodes 115 and 116 can be omitted and heater films 113 can be located on both sides of solid electrolyte 114, as shown in FIG. 4E. In such preferred embodiment, heater films 113 act both as heaters when power is applied to them and as electrodes when signals are read from them.

Thin film oxygen sensors having a silicon nitride bridge or diaphragm connection to a silicon substrate can severely deform due to thermal expansion, which often results in fracture at elevated temperatures. The V-shaped structure according to certain preferred embodiments of this invention uses the cantilever arrangement to relieve thermal expansion stresses. The V-shape also facilitates the anisotropic etching process under dielectric film 112 and provides adequate support for solid electrolyte 114. Solid electrolyte 114 expands in the same direction as dielectric film 112 when solid electrolyte 114 is heated. FIG. 7 shows another embodiment according to this invention having an overall U-shaped structure with serpentine configured heater films 113. FIG. 8 shows yet another embodiment according to this invention, also having an overall V-shaped structure. In FIGS. 6–8, solid electrolyte 114 is located between the legs of the "V" or "U", so that cantilever portion 125 of dielectric layer 112 is suspended over etch pit 130. Cantilever portion 125 permits dielectric layer 112 to expand in the same direction as electrodes 115 and 115, for example when solid electrolyte 114 is heated.

Figure 9:
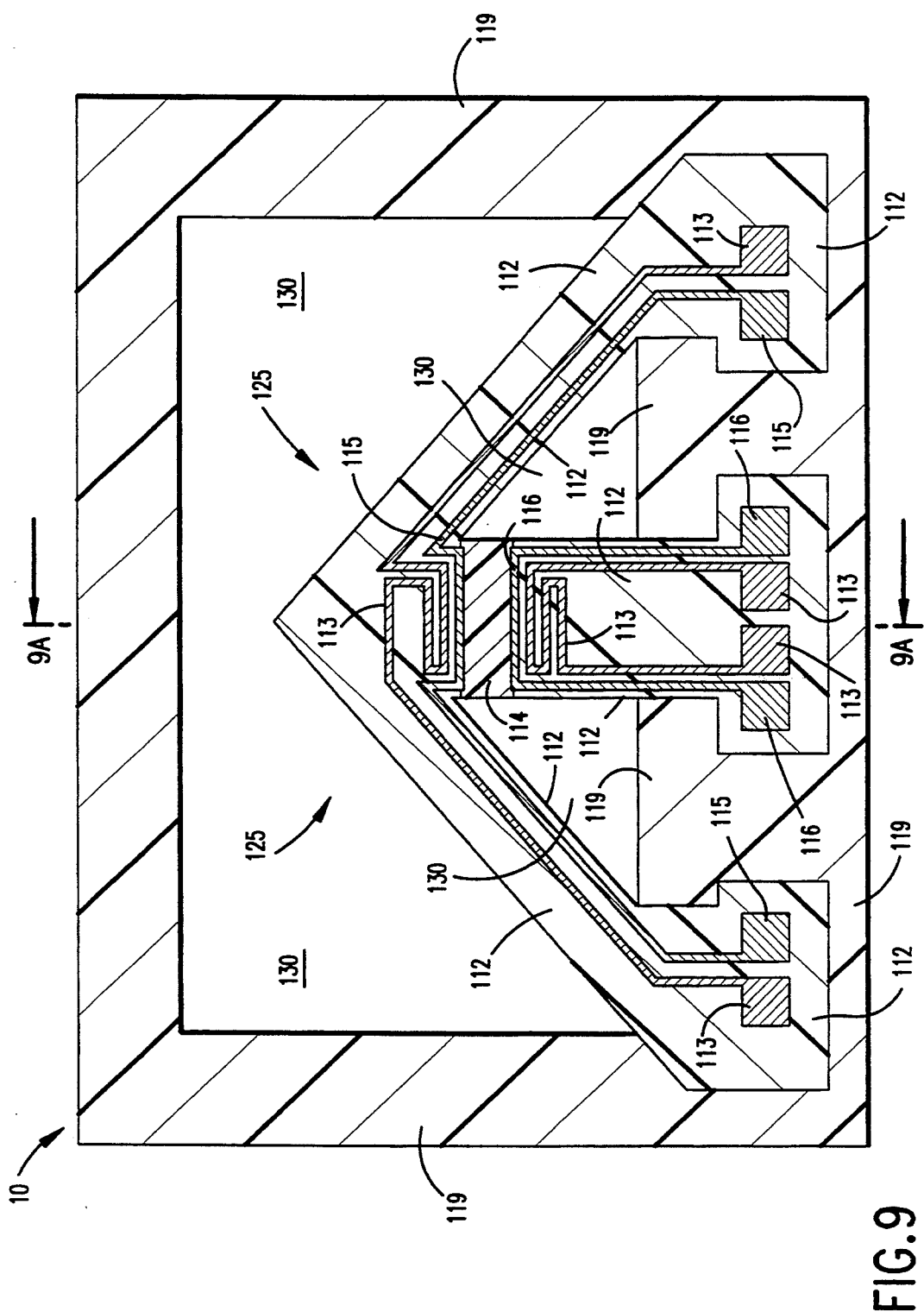
FIG. 9 shows an enlarged plan view of a solid-state oxygen microsensor, with the heater and electrode elements exposed for purposes of drawing clarity, utilizing a generally A-shaped thin film structural configuration according to one preferred embodiment of this invention.
Figure 9A:
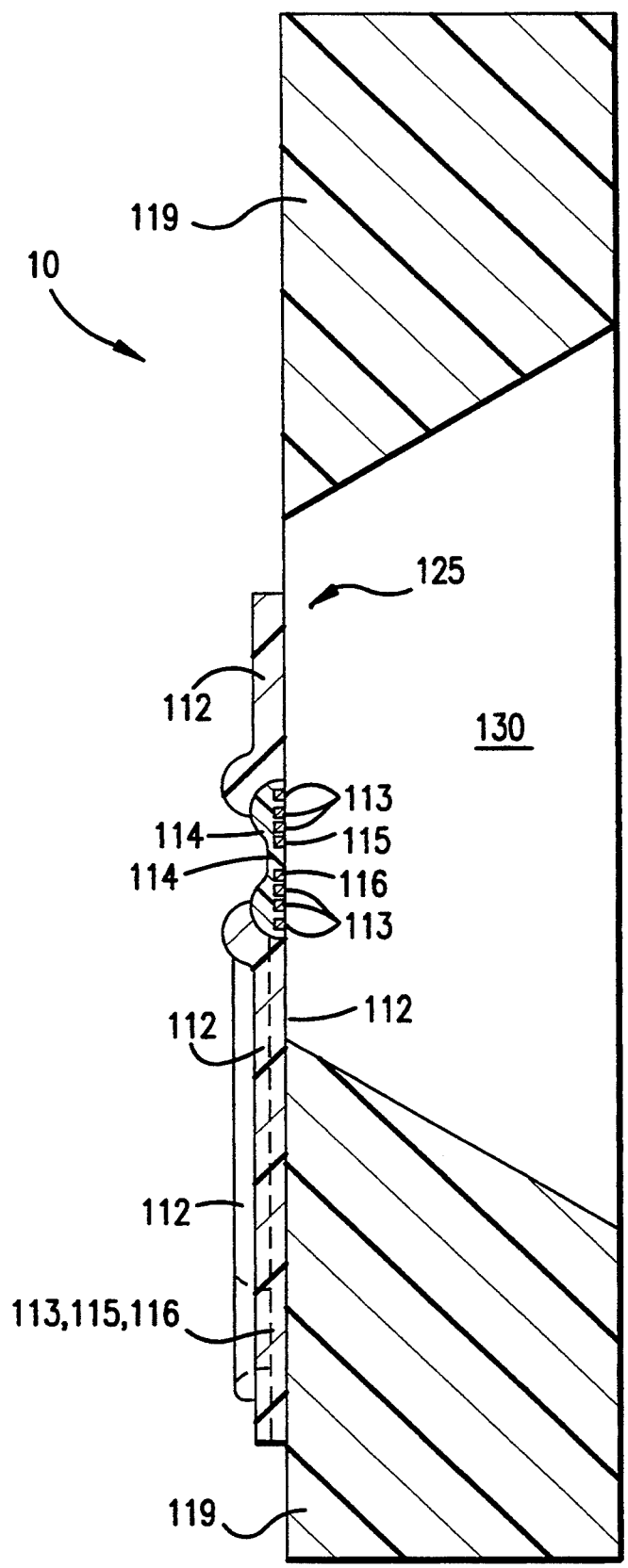
FIG. 9A shows an enlarged cross section, showing the overlaying layers not shown in FIG. 9, along line 9A—9A as shown in FIG. 9.

FIG. 9 shows a thin film oxygen microsensor 10, according to another preferred embodiment of this invention. Cantilever portion 125 forms an overall A-frame structure. Both FIGS. 9 and 9A show solid electrolyte 114 and dielectric layer 112. The A-frame structure accommodates relief of thermal stresses by directing the thermal expansions of dielectric layer 112, electrodes 115 and 116, and heater films 113 in the same direction, into an unconstrained or free space, such as that over etch pit 130. Dielectric layer 112 extends from both sides of oxygen microsensor 10, over one edge of dielectric layer 112 that forms etch pit 130, and thus permits all thermal expansion except the differential thermal expansion to act in the same direction, thereby reducing the stress on solid electrolyte 114.

FIG. 9A shows an enlarged cross-sectional view taken along line 9A—9A, as shown in FIG. 9. Although FIGS. 6–9 do not show such feature, for clarity purposes, FIG. 9A shows one preferred embodiment wherein solid electrolyte 114 overlays heater films 113 and electrodes 115 and 116. Dielectric layer 112 supports heater films 113, solid electrolyte 114, and electrodes 115 and 116 as cantilever portion 125 over etch pit 130. Dielectric layer 112 preferably comprises $Al_2O_3$, $SiO_2$, $Si_3N_4$, MgO or other suitable high temperature insulating materials.

Referring again to FIG. 2, electrodes 15 and 16, and leads 21 and 22 are intended to transmit signals for obtaining sensor temperature differential or temperature gradient measurements across solid electrolyte 114, as well as oxygen concentration measurements. Leads 18 and 17 preferably comprise Pt/10% Rh, palladium or rhodium, or alloys thereof. Switch A is preferably only closed during a temperature differential or temperature gradient measurement. Switch A is preferably open during oxygen concentration measurement, and in such mode the connection of platinum leads 21 and 22 are used to measure the sensor output ($\Delta E$) or potential difference across electrodes 15 and 16. As shown in FIG. 2, leads 21 and 22 are connected to high impedance voltmeter 23 to measure the potentials across solid electrolyte 14. When switch A is closed, the high temperature thermocouple junctions formed by leads 21 and 18 and with leads 22 and 17 are used to measure and determine the temperature differentials or temperature gradients, typically between about 20° C. and about 200° C., of oxygen microsensor 10 at absolute operating temperatures of about 300° C. to about 900° C.

Oxygen ion conducting solid electrolyte 14 which contacts electrodes 15 and 16 may comprise any suitable oxygen ion conducting material, such as $ZrO_2$, $CeO_2$, $Bi_2O_3$, and other metal oxides having similar properties, such as the above $ZrO_2$ suitably doped with calcia or yttria to achieve crystallographic stability and preferred conductivity levels at the operating temperatures of oxygen microsensor 10. Suitable electrolyte materials are well known within the art. Yttria stabilized zirconia (YSZ) is a particularly preferable solid electrolyte. Oxygen ion conducting solid electrolyte 14 preferably comprises a thin membrane which may be applied to the substrate material by techniques which are known within the art, such as ion beam sputtering.

Figure 4F:
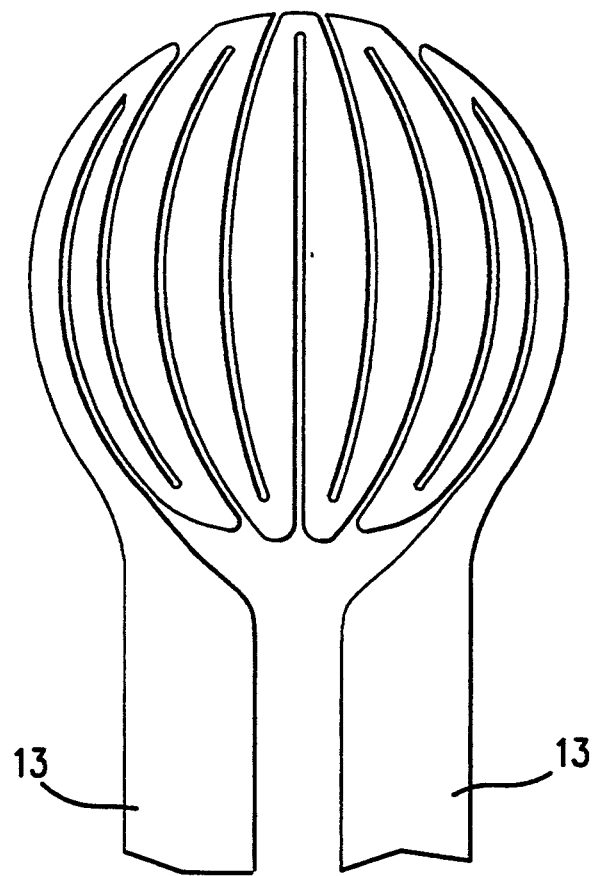

According to one preferred embodiment of this invention, heater film 13 is positioned in close proximity to oxygen ion conducting solid electrolyte 14 and electrodes 15 and 16, and is preferably deposited on the surface of solid electrolyte 14, opposite of electrodes 15 and 16. Preferred heater film 13 configurations are shown in FIGS. 4A–4F, but many other heater configurations which are known within the art would be suitable for use in oxygen microsensor 10 of this invention. The geometrical shapes of heater film 13 as shown in FIGS. 4C, 4D and 4F are preferred when positioning heater film 13 beneath electrode 16 as shown in FIGS. 3A and 3B, so that a uniform, radial temperature gradient can be formed. The geometrical shapes of heater film 13 as shown in FIGS. 4A, 4B and 4E are preferred when positioning heater film 13 beneath electrode 16 as shown in FIGS. 1 and 2. Heater film 13 is energized at terminals 11 and 11A from an external circuit to provide suitable operating temperatures at heater film 13. Heater film 13 preferably comprises Pt, SiC, $SnO_2$, or other suitable materials having similar heat transfer properties. Heater film 13 may have a continuous, uniform film between the pads, as shown in FIG. 4A; a rectangular serpentine configuration with a lower temperature section on the right portion of the serpentine configuration, as shown by the wider section having lower resistance of heater film 113 in FIG. 4B; a rolled serpentine heater configuration as shown in FIG. 4C; a circular serpentine configuration as shown in FIG. 4D; two separated rectangular serpentine heater units as shown in FIG. 4E, or a generally circular wider serpentine configuration as shown in FIG. 4F. The temperature gradient across electrodes 15 and 16 may be generated by two separated heaters energized to provide different absolute temperatures and thereby establish a temperature gradient, or by adjustment of the electrode placement and configuration with respect to heater film 13, to provide the requisite temperature gradient.

Heater film 13 is preferably mounted or embedded within dielectric layer 12, which preferably comprises aluminum oxide or silicon nitride, or can be an integral part of leads 21 and 22, as shown in FIGS. 3B and 4E. Leads 21 and 22 of FIG. 4E are shown serving a dual role, each with heater film 13. Thus, certain pads are identified in FIG. 4E as "21, 13" and "22, 13" and one pad is identified as "22, 13" in FIG. 3B for the same reason. As shown in FIG. 4E, heater films 13 and 13A represent two independent heater films. Also, with respect to but not shown in FIG. 4E, one of the two serpentine configurations floats or is electrically ungrounded so that measurement readings can be taken. Heater film 13 may be embedded within a single dielectric layer 12, as shown in FIG. 1, or may be sandwiched between two thin dielectric layers 12. Dielectric layer 12 provides support for the layer of solid electrolyte 14 and insulates heater film 13 from interaction with the sensor electrodes 15 and 16, thus extending its operating lifetime.

Operation of the solid-state oxygen microsensor according to the process of one preferred embodiment of the present invention will be described with reference to FIG. 2. Heater film 13 is initially energized to raise the temperature of oxygen microsensor 10 to suitable operating ranges and to establish a known and preferably constant temperature gradient across electrodes 15 and 16. When switch A is closed, electrical contact is established between electrodes 15 and 16 and a temperature differential measurement device, such as high impedance voltmeter 23. By opening switch A, output signals from electrodes 15 and 16 are conveyed to high impedance voltmeter 23 which measures the EMF and to processor 24. Processor 24 can be any suitable processor means or computer, apparent to those skilled in the art, for calculating a partial pressure of oxygen when given a constant temperature gradient value and a corresponding sensor output ($\Delta E$) value at such temperature gradient value. Based upon the measurement of EMF and a known temperature differential across electrodes 15 and 16, processor 24 is used to determine or compute the partial pressure of oxygen in the ambient atmosphere, based upon a program containing data and known functions from the sensor output ($\Delta E$) and the known temperature differential or temperature gradient across solid electrolyte 114. According to one preferred embodiment of this invention, processor 24 is programmed to contain the functional relationships between the sensor output ($\Delta E$), the temperature gradient, and the partial pressure of oxygen, preferably as shown in FIG. 5B, or even FIG. 5A.

The temperature gradient across electrodes 15 and 16 must be maintained at a constant value only until a corresponding sensor output ($\Delta E$) measurement is taken at such known temperature gradient. If both measurements, the temperature gradient value and the sensor output value, can be taken simultaneously, then it is not necessary to maintain the temperature gradient at the constant value. If the temperature differential maintained across the electrodes can be stabilized so that the temperature differential remains at a constant value, then measurement of the actual temperature differential would no longer be necessary, and the partial pressure of oxygen could be determined, for example by processor 24, solely as a function of the sensor output ($\Delta E$).

Figure 5A:
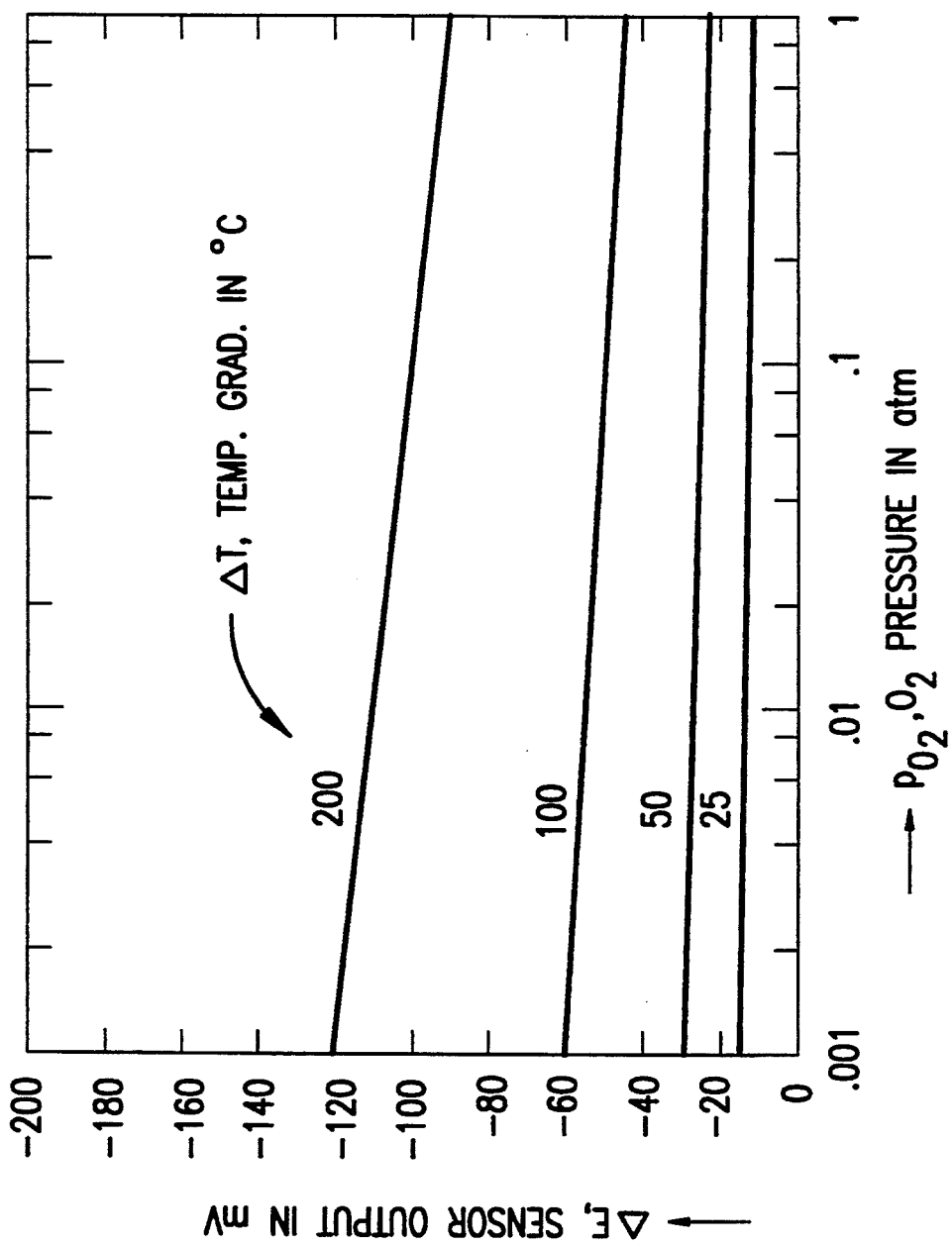
FIG. 5A illustrates a known theoretical relationship between oxygen partial pressure, a sensor output ($\Delta E$) and a temperature gradient generated across the electrodes during operation of the oxygen microsensor, according to the present invention.
Figure 5B:
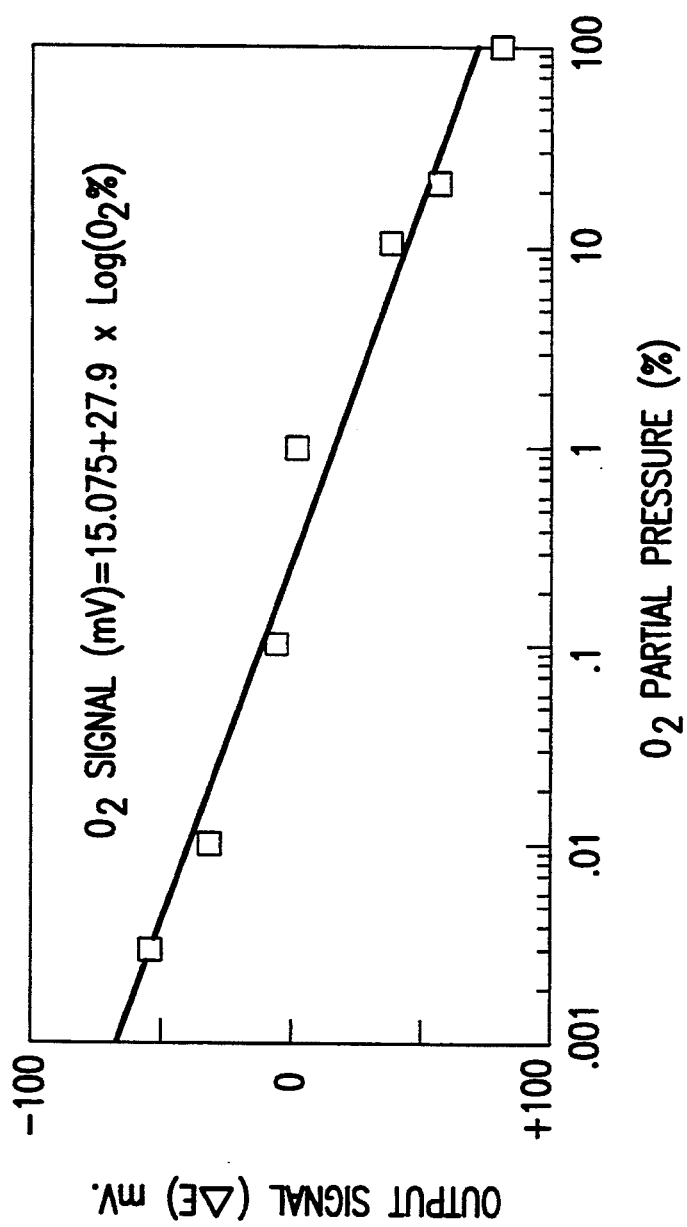
FIG. 5B illustrates an experimentally derived relationship, according to results obtained with a prototype oxygen microsensor of this invention, between oxygen partial pressure, a sensor output ($\Delta E$) and a constant temperature gradient generated across electrodes during operation of the oxygen microsensor.

FIG. 5B shows the relationship between the sensor output, the temperature differential, and the partial pressure of oxygen in the ambient atmosphere, based upon experimental data according to this invention. FIG. 5A shows a similar relationship generated from known Seebeck coefficient data, i.e. thermoelectric potential data published by Fadeev et al: "Thermo-EMF of Cells with a $ZrO_2+Y_2O_3$ Electrolyte in Atmospheres of Different Compositions", Soc. Electrochem (USA), Vol. 18, No. 7, p. 894 (1982).

It is apparent that many elements shown in the various drawings and previously described in this specification, such as dielectric layers 12 and 112, heaters 13 and 113, solid electrolytes 14 and 114, and electrodes 15, 16, 115 and 116 are interchangeable between the various embodiments.

The configuration of oxygen microsensor 10 of the present invention has been described generally above without reference to specific or relative dimensions. Preferred dimensions depend, of course, upon the specific application and components. In general, however, solid electrolyte 14 and 114 may be from about 200 to about 1000 $\mu m$ in length, by 10 to about 1000 $\mu m$ in width, preferably in a rectangular or circular pattern, and has a thickness of about 0.2 to about 20 $\mu m$, preferably about 0.3 to about 2 $\mu m$. Electrodes 15 and 16, according to the embodiments shown in FIGS. 3A and 3B, for example, have an interelectrode spacing of about 5 to about 100 $\mu m$, preferably about 10 to about 40 $\mu m$, and have a thickness of about 500 to about 3000 Å, preferably about 750 to about 1500 Å. The dimensions of heaters 13 and 113 correspond generally to the dimensions such that their resistance ranges from about 100 to 1000 ohms.

Figure 10:
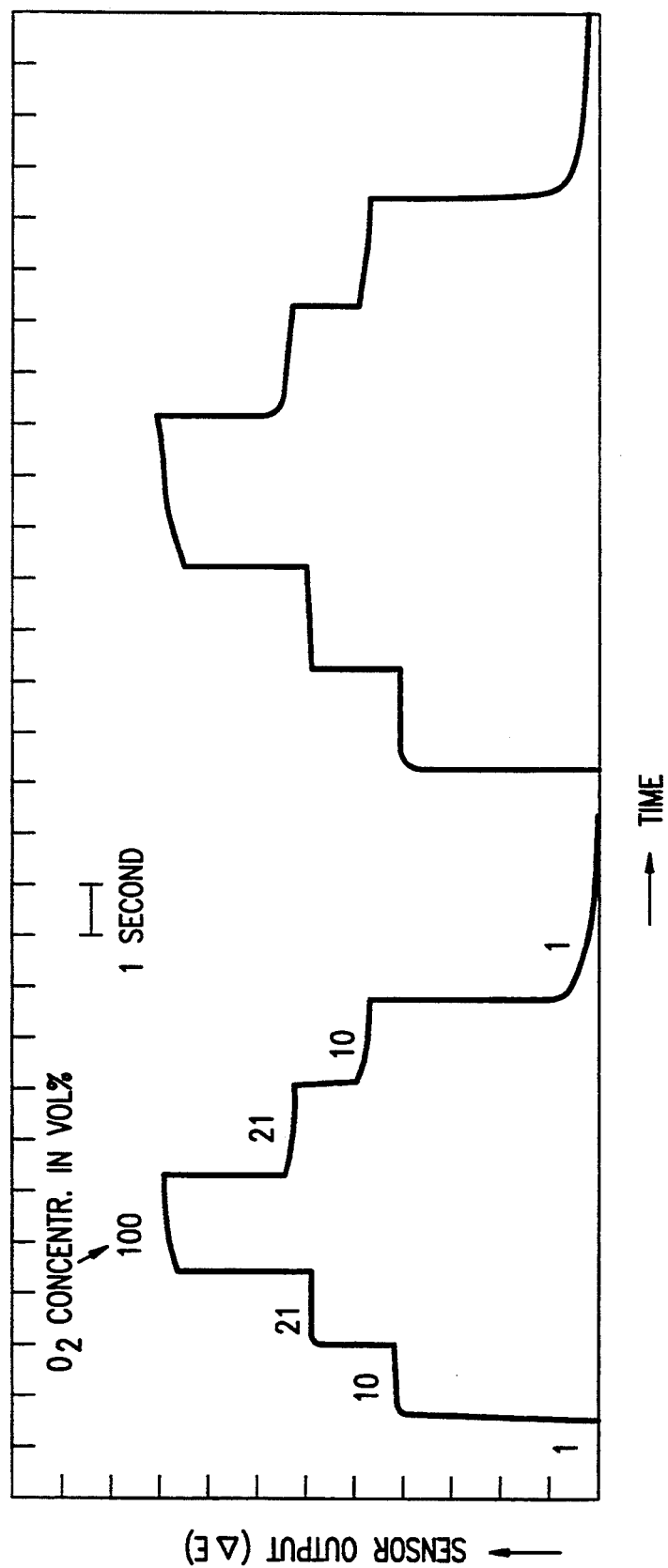
FIG. 10 shows a graph chart of time vs. sensor output ($\Delta E$) for various oxygen concentrations between 1% and 100%.

FIG. 10 shows experimental results obtained with oxygen microsensor 10 according to this invention. The curve represents a step by step response to varying oxygen concentrations from 1% to 100% and then back to 1%. The response time is less than one second and some trailing response is shown at the lowest concentration levels.

The temperature gradient was maintained at about 150° C. by energizing two heaters across the $ZrO_2$ film by two different, isolated power supplies only one of which was grounded. Oxygen microsensor 10 was fabricated so that the silicon substrate supported the $Si_3N_4$ film, which in turn supported the zirconia sensor film, and thus reduced undesirable stresses caused by mismatches in thermal coefficients of expansion. The center of the structure was heated to greater than approximately 700° C.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A solid-state oxygen microsensor comprising:
   an oxygen ion conducting solid electrolyte;
   a pair of co-planar, independent sensor electrodes exposed to a single ambient atmosphere, said coplanar independent sensor electrodes spaced apart from each other and contacting said solid electrolyte;
   heater means for heating each said sensor electrode to a different absolute operating temperature and thereby generating a temperature gradient across said electrodes, said heater means comprising a heater film which is in direct contact with at least one of said solid electrolyte and a dielectric layer of the oxygen microsensor;

temperature gradient control means for maintaining said temperature gradient at a constant value;

temperature measuring means for measuring a temperature gradient across said co-planar, independent sensor electrodes;

voltage measuring means for measuring an output voltage potential difference across said co-planar, independent sensor electrodes;

temperature gradient control means for maintaining said temperature gradient at a constant value at least until a corresponding said output voltage potential difference is measured; and processor means in communication with said temperature measuring means and said voltage measuring means for determining an oxygen partial pressure of said single ambient atmosphere based upon said temperature gradient and said corresponding output voltage potential difference at said temperature gradient.

2. A solid-state oxygen microsensor according to claim 1, wherein said heater means is capable of maintaining each of said electrolyte and said sensor electrodes at an absolute operating temperature between about 300° C. to about 900° C.

3. A solid-state oxygen microsensor according to claim 1, wherein said heater means is capable of generating said constant value of said temperature gradient at about 20° C. to about 200° C.

4. A solid-state oxygen microsensor according to claim 1, wherein a portion of said dielectric layer forms a cantilever portion which extends over an etch pit.

5. A solid-state oxygen microsensor according to claim 4, wherein said cantilever portion of said dielectric layer supports a portion of each of said co-planar, independent sensor electrodes.

6. A solid-state oxygen microsensor according to claim 4, wherein said heater means further comprise at least one thin layer structure and said dielectric layer supports at least a portion of each said thin layer structure.

7. A solid-state oxygen microsensor according to claim 6, wherein said cantilever portion comprises said co-planar, independent sensor electrodes, said electrolyte and all said thin layer structures generally forming a V-shaped structure.

8. A solid-state oxygen microsensor according to claim 6, wherein said cantilever portion comprises said co-planar, independent sensor electrodes, said electrolyte and all said thin layer structures generally forming an overall A-shaped structure.

9. A solid-state oxygen microsensor according to claim 1 wherein said co-planar, independent sensor electrodes are about 500 to about 3000 Å thick; said co-planar, independent sensor electrodes are selected from the group consisting of platinum, palladium, rhodium, and iridium; and said co-planar, independent sensor electrodes are spaced about 5 to about 100 $\mu$m from one another.

10. A solid-state oxygen microsensor according to claim 1 wherein a surface area of said electrolyte is about 200 to about 1000 square $\mu$m; said electrolyte is about 0.2 to about 20 $\mu$m thick; and said electrolyte is selected from the group consisting of $ZrO_2$, $CeO_2$ and $Bi_2O_3$.

11. A solid-state oxygen microsensor according to claim 1 wherein said dielectric layer is positioned between said co-planar, independent sensor electrodes and at least one heater electrode of said heater means.

12. A solid-state oxygen microsensor according to claim 1 wherein said heater means further comprise: a pair of leads and each said lead connected to a corresponding said co-planar, independent sensor electrode.

13. A solid-state oxygen microsensor according to claim 1 wherein at least one said co-planar, independent sensor electrode is electrically connected to serve a dual role as a sensor signal carrier during a measuring mode of the solid-state oxygen microsensor and as a heater during a heating mode of the solid-state oxygen microsensor.

14. A solid-state oxygen microsensor according to claim 1 wherein said co-planar, independent sensor electrodes are geometrically symmetric.

15. A solid-state oxygen microsensor according to claim 1 further comprising: one said co-planar, independent sensor electrode having a generally arcuate shape, the other said co-planar, independent sensor electrode having a generally circular shape, and said generally circular shaped co-planar, independent sensor electrode positioned to maintain a constant distance between an internal surface of said generally arcuate shape and an external surface of said generally circular shape.

* * * * *

UNITED STATES PATENT AND TRADEMARK OFFICE
CERTIFICATE OF CORRECTION

PATENT NO. : 5,389,225
DATED : 14 February 1995
INVENTOR(S) : Roger L. AAGARD et al.

It is certified that error appears in the above-identified patent and that said Letters Patent is hereby corrected as shown below:

On line 2 of the title, after "THIN" please insert --FILM--.

Signed and Sealed this

Thirtieth Day of May, 1995

Attest:

BRUCE LEHMAN

Attesting Officer     Commissioner of Patents and Trademarks